United States Patent
Nakagawa et al.

(10) Patent No.: US 6,756,497 B1
(45) Date of Patent: Jun. 29, 2004

(54) BENZOIC ACID DERIVATIVES AND PROCESSES FOR THE PREPARATION THEREOF

(75) Inventors: Yuuki Nakagawa, Kanagawa (JP); Masao Yamaguchi, Kanagawa (JP); Hiroyuki Adachi, Kanagawa (JP); Hiroyuki Yamanaka, Kanagawa (JP); Tomio Yagihara, Kanagawa (JP); Masami Hatano, Kanagawa (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 09/720,825

(22) PCT Filed: Jul. 13, 1999

(86) PCT No.: PCT/JP99/03773

§ 371 (c)(1),
(2), (4) Date: Jan. 12, 2001

(87) PCT Pub. No.: WO00/03988

PCT Pub. Date: Jan. 27, 2000

(30) Foreign Application Priority Data

| Jul. 14, 1998 | (JP) | 10-199125 |
| Jul. 14, 1998 | (JP) | 10-199126 |
| Mar. 11, 1999 | (JP) | 11-064856 |
| Apr. 28, 1999 | (JP) | 11-122939 |

(51) Int. Cl.[7] ........ C07D 239/02; C07D 513/22; C07D 263/02; C07D 493/00; C07C 321/00
(52) U.S. Cl. ........ 544/242; 548/148; 548/215; 548/240; 548/247; 548/356.1; 546/26; 568/24; 568/25; 568/26; 568/439; 568/591; 549/337
(58) Field of Search ............. 548/215, 148, 548/247, 240, 356.1, 235; 546/26; 544/242; 568/439, 25, 24, 26, 591; 549/337

(56) References Cited

U.S. PATENT DOCUMENTS

| 3,625,977 A | | 12/1971 | Hamb | 260/340.7 |
| 4,643,757 A | * | 2/1987 | Baba et al. | 71/86 |
| 4,966,869 A | | 10/1990 | Lee | 562/869 |
| 5,834,402 A | * | 11/1998 | Von Deyn et al. | 504/271 |
| 5,948,917 A | * | 9/1999 | Adachi et al. | 548/247 |

FOREIGN PATENT DOCUMENTS

WO  WO 96/26206  * 8/1996

OTHER PUBLICATIONS

Mitchell et al, an approach utilizing a diels–alder route to 1,2,3–trisubstituted benzenes, Apr. 1985, Tetrahedron, 42, 1741–42.*

Hoch, a study of the acid and bse hydrolysis of bridged ketones, Nov. 1960, J. of Organic Chem., 26, 2066–71.*

Mitchell et al.; Cis–dimethyldihydropyrene synhesis. An Approach Utilizing a Diels–Alder Route to 1,2,3–Trisubstituted Benzenes.; Tetrahedron, vol. 42, No. 6, p. 1741–1744 (1986).

Mark; Nonstereospecific Diels–Alder Reactions. I. Reaction of Hexachlorocyclopentadiene with 1,2–Disubstituted Ethylenes. J. Org. Chem., vol. 39, No. 21, p. 3179–3181 (1974).

Hoch; A Study of the Acid and Base Hydrolysis of Bridged Ketones Derived from Diels–Alder Adducts of 1,2,3,4–Tetrachloro–5,5–dimethoxycyclopentadiene, Chem. & Ind., 110 (1958), vol. 26 p. 2066–2072.

* cited by examiner

*Primary Examiner*—D. Margaret Seaman
*Assistant Examiner*—Taylor V Oh
(74) *Attorney, Agent, or Firm*—Jacobson Holman PLLC

(57) ABSTRACT

Benzoic acid derivatives useful as intermediates for the preparation of drugs and agricultural chemicals, particularly compounds having herbicidal activity; and easy and economical processes for the preparation of the same. The processes are specifically those represented by reaction formula for the preparation of compounds represented by general formulae (1) and (6).

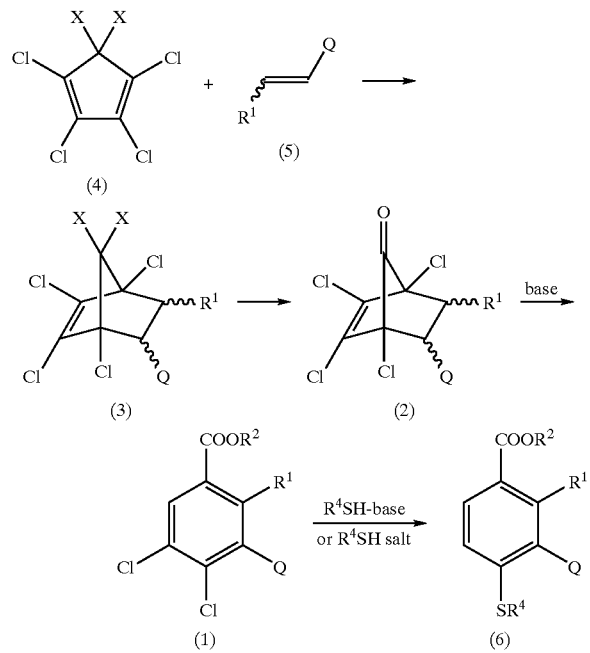

5 Claims, No Drawings

BENZOIC ACID DERIVATIVES AND PROCESSES FOR THE PREPARATION THEREOF

FIELD OF THE INVENTION

The present invention relates to benzoic acid derivatives useful as intermediates for the preparation of drugs and agricultural chemicals, particularly compounds having herbicidal activity, and to processes for the preparation thereof.

BACKGROUND ART

A method (A) of obtaining benzoic acid derivatives by reactions represented by the following reaction scheme,

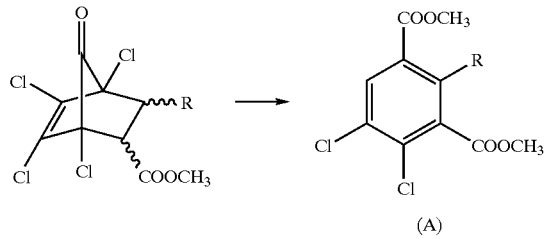

(A)

between bicycloheptenone derivatives substituted with carboxylates and alcolates or the like is described in Tetrahedron, 42, 1741 (1986) and J. Org. Chem., 26, 2066 (1961).

However, there are no reports on reactions of bicycloheptenone derivatives substituted with hetero rings.

Known methods of dehalogenation of aromatic halogenated compounds include, for example, catalytic hydrogenolysis using palladium-carbon or Raney nickel as a catalyst, a method of using metal and metal salts such as lithium or sodium, hydrogenolytic reduction with tin hydride, reduction with metal-hydrogen complex compounds such as lithium aluminum hydride, and electrolytic reduction, which are described in Shin Jikkenkagakukouza, Vol. 14, Syntheses and Reactions of Organic Compounds [I] pages 22–30 (edited by the Chemical Society of Japan, published by Maruzen Co., Ltd.).

DISCLOSURE OF THE INVENTION

Substituted benzoic acid compounds, such as 4-alkylthiobenzoic acid derivatives, are important as intermediates for the preparation of agricultural chemicals and drugs. It has been desired to develop easy and industrially advantageous processes for the preparation of the said benzoic acid derivatives.

The present invention is directed to (a) a benzoic acid derivative represented by Formula (1)

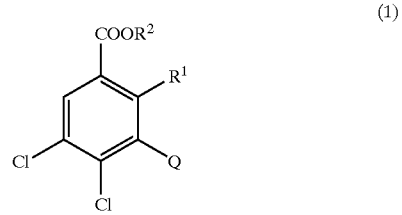

(1)

(wherein $R^1$ is hydrogen or $C_{1-4}$ alkyl,
$R^2$ is hydrogen or $C_{1-6}$ alkyl, and Q is an optionally substituted, saturated or unsaturated, 5- or 6-membered heterocyclic group containing 1 to 4 N, O or S atoms and combining with the benzene ring via a carbon atom);

(b) a process for the preparation of a benzoic acid derivative of the said Formula (1), characterized by acting a base on a bicycloheptenone derivative of Formula (2)

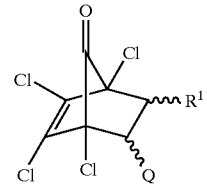

(2)

(wherein $R^1$ and Q are as defined above), in an appropriate solvent;

(c) a process for the preparation of a benzoic acid derivative of the said Formula (1), characterized by consisting of a stage of preparing a bicycloheptenone derivative of the said Formula (2) by hydrolysis of a bicycloheptene derivative of Formula (3)

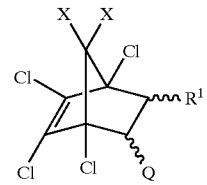

(3)

(wherein $R^1$ are as defined above, and X is chlorine or $C_{1-4}$ alkoxy and two X's may join to form a $C_{2-3}$ alkylenedioxy group optionally substituted with $C_{1-4}$ alkyl), and of acting a base and water or alcohol on a bicycloheptenone derivative of the said Formula (2) in an appropriate solvent;

(d) a process for the preparation of a bicycloheptene derivative of the said Formula (3), characterized by reacting a cyclopentadiene derivative of Formula (4)

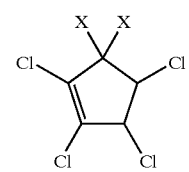

(4)

(wherein X is as defined above) with an ethylene derivative substituted with a hetero ring, of Formula (5)

(5)

(wherein $R^1$ and Q are defined above);

(e) a bicycloheptenone derivative of the said formula (2); and (f) a process for the preparation of a benzoic acid derivative of Formula (6)

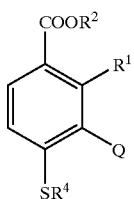

(6)

(wherein $R^1$, $R^2$ and Q are as defined above and $R^4$ is $C_{1-6}$ alkyl), characterized by reacting a 4,5-dichlorobenzoic acid derivative of the said Formula (1), with a mercaptan of Formula $R^4SH$ (wherein $R^4$ is as defined above) and a base or with a salt of mercaptan of Formula $R^4SH$ (wherein $R^4$ is as defined above)

In the definitions of the compounds of the said Formulae (1) and (2), which are the compounds of the present invention, the compounds of Formula (3) of their precursors and the compounds of Formula (6), $R^1$ is hydrogen, or $C_{1-4}$ alkyl such as methyl, ethyl, propyl, isopropyl n-butyl isobutyl s-butyl or t-butyl;

a $R^2$ is hydrogen, or $C_{1-6}$ alkyl such as methyl, ethyl, propyl, isopropyl, n-butyl, isobutyl, s-butyl t-butyl, n-pentyl, isopentyl, neopentyl, n-hexyl or isohexyl;

X is halogen such as chlorine, or $C_{1-4}$ alkoxy such as methoxy, ethoxy, propoxy, isopropoxy or butoxy;

Two X's may join to form a $C_{2-3}$ alkylenedioxy group, such as ethylenedioxy or trimethylenedioxy;

Further, the said $C_{2-3}$ alkylenedioxy group may be substituted with $C_{1-4}$ alkyl such as methyl, ethyl, propyl, isopropyl, n-butyl, isobutyl, s-butyl and t-butyl; and Q is an optionally substituted, saturated or unsaturate 5- or 6-membered heterocyclic group containing 1 to 4 N, O or S atoms and combining with the benzene or bicycloheptane ring via a carbon atom.

Such hetero rings include, for example, 5-membered heterocyclic groups containing 1 to 4 N, O or S atoms, such as 2-furyl, 3-furyl,
2-thienyl, 3-thienyl,
2,3-dihydrofuran-2-yl, 2,3-dihydrofuran-3-yl, 2,3-dihydrofuran4-yl,2,3-dihydrofuran-5-yl, 2,5-dihydrofuran-2-yl, 2,5-dihydrofuran-3-yl,
2,3-dihydrothiophen-2-yl, 2,3-dihydrothiophen-3-yl, 2,3-dihydrothiophen-4-yl, 2,3-dihydrothiophen-5-yl, 2,5-dihydrothiophen-2-yl, 2,5-dihydrothiophen-3-yl,
pyrrol-2-yl, pyrrol-3-yl,
imidazol-2-yl, imidazol-4-yl, imidazol-5-yl,
2-imidazolin-2-yl, 2-imidazolin-4-yl, 2-imidazolin-5-yl,
pyrazol-3-yl, pyrozol-4-yl, pyrazol-5-yl,
oxazol-2-yl, oxazol-4-yl, oxazol-5-yl,
isoxazol-3-yl, isoxazol-4-yl, isoxazol-5-yl.
1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl,
4-thiazolyl, 4-thiazolyl, 5-thiazolyl,
isothiazol-3-yl, isothiazol-4-yl, isothiazol-5-yl,
1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl,
1,2,4-triazol-3-yl, 1,2,4-triazol-5-yl, 1,3,4-triazol-2-yl, 1,2,3-triazol-4-yl, 1,2,3-triazol-5-yl, tetrazol-5-yl,
2-pyrrolin-1-yl, 2-pyrrolin-2-yl, 2-pyrrolin-3-yl, 2-pyrrolin4-yl, 2-pyrrolin-5-yl,
2-oxazolin-2-yl, 2-oxazolin-4-yl, 2-oxazolin-5-yl, 3-oxazolin-2-yl, 3-oxazolin-4-yl, 3-oxazolin-5-yl, 4-oxazolin-2-yl, 4-oxazolin-4-yl, 4oxazolin-5-yl,
2-isoxazolin-3-yl, 2-isoxazolin-4-yl, 2-isoxazolin-5-yl, 3-isoxazolin-3-yl, 3-isoxazolin-4-yl, 3-isoxazolin-5-yl, 4-isoxazolin-3-yl, 4-isoxazolin-4-yl, 4-isoxazolin-5-yl,
2-thiazolin-2-yl, 4-thiazolin-4-yl, 4-thiazolin-5-yl,
2-isothiazolin-3-yl, 2-isothiazolin-4-yl, 2-isothiazolin-5-yl, 3-isothiazolin-3-yl, 3-isothiazolin-4-yl, 3-isothiazolin-5-yl, 4-isothiazolin-3-yl, 4-isothiazolin-4-yl, 4-isothiazolin-5-yl,
1-pyrazolin-3-yl, 1-pyrazolin-4-yl, 1-pyrazolin-5-yl, 2-pyrazolin-3-yl, 2-pyrazolin-4-yl, 2-pyrazolin-5-yl, 3-pyrazolin-3-yl, 3-pyrazolin-4-yl and 3-pyrazolin-5-yl;
saturated 5-membered heterocyclic groups containing 1 to 4 N, O or S atoms, such as
2-pyrrolidinyl, 3-pyrrolidinyl,
2-tetrahydrofuranyl, 3-tetrahydrofuranyl,
2-tetrahydrothienyl, 3-tetrahydrothienyl,
2-oxazolidinyl, 4-oxazolidinyl, 5-oxazolidinyl,
3-isoxazolidinyl, 4-isoxazolidinyl, 5-isoxazolidinyl,
2-thiazolidinyl, 4-thiazolidinyl, 5-thiazolidinyl,
3-isothiazolidinyl, 4-isothiazolidinyl, 5-isothiazolidinyl,
2-imidazolidinyl, 4-imidazolidinyl,
1,2,4-oxadiazolidin-3-yl, 1,2,4-oxadiazolidin-5-yl, 1,3,4-oxadiazolidin-2-yl,
1,2,4-thiadiazolidin-3-yl, 1,2,4-thiadiazolidin-5-yl, 1,3,4-thiadiazolidin-2-yl,
1,3,4-triazolidin-2-yl,
1,3-dioxolan-2-yl, 1,3-dioxolan-4-yl,
1,3-dithiolan-2-yl, 1,3-dithiolan-4-yl, and
1,3-oxathiolan-2-yl; and 6-membered heterocyclic groups containing 1 to 4 N, O or S atoms, such as 2-pyridyl, 3-pyridyl, 4-pyridyl,
3-pyridazinyl, 4-pyridazinyl,
2-pyrimidinyl, 4-pyrimidinyl, 5-pyrimidinyl,
pyrazin-2-yl,
2H-pyran-3-yl, 2H-thiopyran-3-yl,
2-piperidinyl, 3-piperidinyl, 4-piperidinyl
2-piperadinyl,
2-morpholinyl, 3-morpholinyl,
5,6-dihydro-4H-1,3-thiazin-2-yl,
2-tetrahydropyranyl, 3-tetrahydropyranyl, 4-tetrahydropyranyl,
2-tetrahydrothiopyranyl, 3-tetrahydrothiopyranyl and 4-tetrahydrothiopyranyl.

These groups may have one or more, same or different, substituents at arbitrary positions of the hetero rings. Such substituents include, for example, $C_{1-4}$ alkyl such as methyl, ethyl, propyl isopropyl, n-butyl, isobutyl, s-butyl and t-butyl, and $C_{1-4}$ haloalkyl such as chloromethyl, dichloromethyl, trichloromethyl, fluoromethyl, difluoromethyl, trifluoromethyl, 1-fluoroethyl, 1,1-difluoroethyl, 2,2,2-trifluoroethyl and pentafluoroethyl.

Q is more preferably one of the following groups represented by Q-1 to Q-9.

Q-1

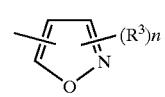

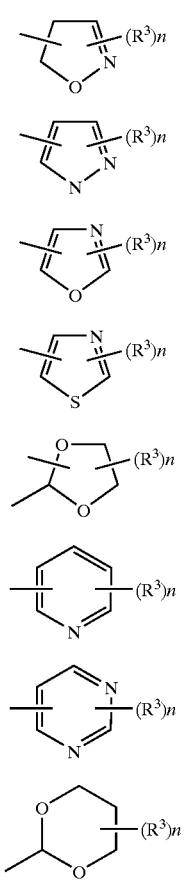

In the above formulae, $R^3$ is, for example, $C_{1-4}$ alkyl such as methyl, ethyl, propyl, isopropyl, n-butyl, isobutyl, s-butyl or t-butyl, or $C_{1-4}$ haloalkyl such as chloromethyl, dichloromethyl, trichloromethyl, fluoromethyl, difluoromethyl, trifluoromethyl, 1-fluoroethyl, 1,1-difluoroethyl, 2,2,2-trifluoroethyl or pentafluoroethyl, and n is 0 or an integer of 1 or 2.

Further, in the said Formula (6), $R^4$ is $C_{1-6}$ alkyl such as methyl, ethyl, propyl, isopropyl, n-butyl, isobutyl s-butyl, t-butyl, n-pentyl, isopentyl, neopentyl, n-hexyl or isohexyl.

The compounds of the present invention, represented by the said Formulae (2) and (3), may have stereoisomers, depending on substituents at positions 5 and 6. They are all covered by the present invention.

IMPLEMENTATION OF THE INVENTION

The compounds of the present invention may be produced by the following processes:

(Process 1) Process for the Preparation of a 4,5-dichlorobenzoic Acid Derivative from a Bicycloheptenone Derivative

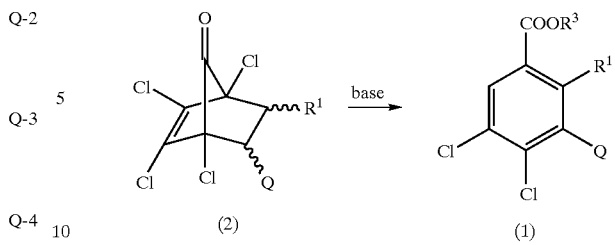

(wherein $R^1$, $R^2$ and Q are as defined above).

A bicycloheptenone derivative (2) of Formula (2) is reacted with a base and water or alcohol in an appropriate solvent to give a compound of Formula (1).

Bases used for this reaction include, for example, alkali metal alcolates such as sodium methylate, sodium ethylate and potassium t-butoxide; alkali metal hydroxides such as sodium hydroxide and potassium hydroxide; alkaline earth metal hydroxides such as calcium hydroxide; alkali metal carbonates such as sodium carbonate, potassium carbonate and sodium hydrogen carbonate; and alkaline earth metal carbonates.

An amount of a base used is preferably 2 to 5 equivalents to 1 mole of a bicycloheptenone derivative (2).

Solvents able to be used for the reaction include alcohols such as methanol, ethanol, propanol, isopropanol, butanol and t-butanol; ethers such as diethyl ether and tetrahydrofuran (THF); hydrocarbons such as benzene and toluene; acetonitrile, dimethylformamide (DMF), water, toluene, benzene and the like, or mixtures of 2 or more of these solvents.

In the aforementioned reaction, it is particularly preferable to use alcoholic solvents, that is, alcohols, or mixed solvents of alcohol and other solvents such as water and alcohol or alcohol and ether.

In the above reaction, an ester ($COOR^2$) having a portion corresponding to an alcohol ($R^2OH$) used or the alkoxide portion of a metal alkoxide ($MOR^2$) used can be obtained; for example, a methyl ester is obtained with the use of methyl alcohol and an ethyl ester from ethyl alcohol.

More preferred combinations of a base and a solvent include, for example, sodium methoxide and methanol (or a mixed solvent of methanol and other solvents), sodium ethoxide and ethanol (or a mixed solvent of ethanol and other solvents), sodium hydroxide and alcohol (or a mixed solvent of alcohol and other solvents), potassium hydroxide and alcohol (or a mixed solvent of alcohol and other solvents), and potassium t-butoxide and butanol.

In the case of the use of mixed solvents or aqueous solvents, carboxylic acids ($R^2$=H) can be obtained. Solvents used together with water are favorably alcohols and ethers. As for bases, the aforementioned hydroxides or carbonates are preferably used.

In the case of the use of metal alkoxides, it is preferable to use corresponding alcohols, as described above. It is of course possible to use other alcohols.

Preferred reaction temperatures are between −10° C. and the boiling point of solvents used.

(Process 2)

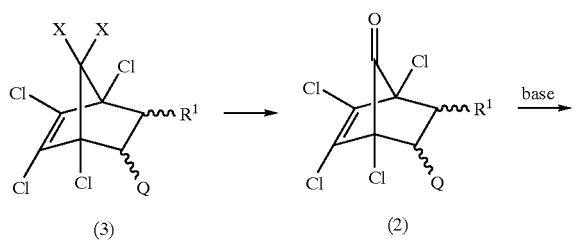

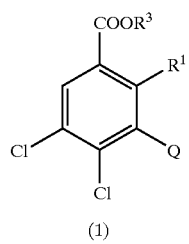

(wherein $R^1$, $R^2$, Q and X are as defined above.)

A bicycloheptenone derivative (2) can be obtained by hydrolysis of a bicycloheptene derivative (3) with an acid such as hydrochloric acid or sulfuric acid.

That is, a compound (2) can be obtained by hydrolyzing a compound (3) without using a solvent or with a solvent including alcohols such as methanol, ethanol and t-butanol, ethers such as diethyl ether and tetrahydrofuran (THF) or aromatic hydrocarbons such as benzene and toluene, or a mixed solvent of two or more of these solvents, at temperature between –10° C. and the boiling point of solvents used.

After this, a target benzoic acid derivative can be prepared in the same way as that described in Process 1 above.

(Process 3)

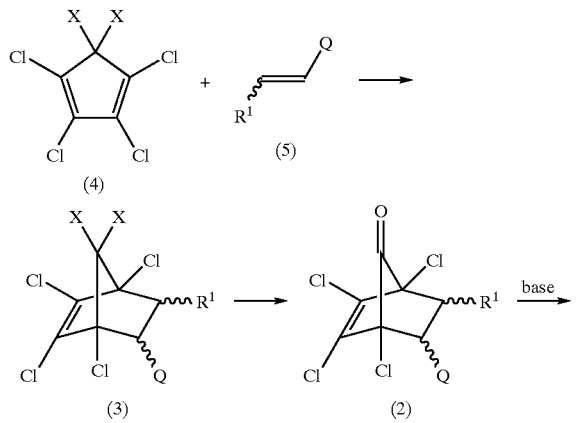

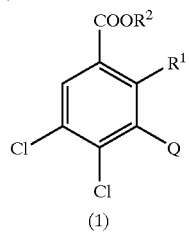

(wherein $R^1$, $R^2$, Q and X are as defined above.)

A Diels-Alder reaction of a cyclopentadiene derivative (4) and an ethylene derivative substituted with a hetero ring (5) gives a bicycloheptene derivative (3).

The Diels-Alder reaction can be carried out according to methods described, for example, in Tetrahedron, 42, 1741–1744 (1986) or J. Org. Chem., 26, 2066–2072 (1961).

In the above reaction, cyclopentadienes and ethylene derivatives are reacted while heating. A molar ratio of the ethylene derivatives used in the reaction is 0.5 to 10 times in equivalent, preferably 1 to 3 equivalents, to 1 mole of cyclopentadienes. The reaction is carried out at temperature between room temperature and 25° C., more preferably between 70° C. and 200° C.

Although this reaction is usually carried out without solvents, solvents may be used. Examples of solvents used include aromatic hydrocarbons such as benzene, toluene, xylene, chlorobenzene and dichlorobenzene; alcohols such as ethanol, n-propyl alcohol, ethylene glycol, 1,3-butanediol and ethylene glycol monomethyl ether; ethers such as dimethoxyethane, dioxane and diethylene glycol dimethyl ether; amides such as N,N-dimethylformamide, N,N-dimethylacetamide, N-methylpyrolidone and N,N-dimethylimidazoline; hydrocarbons containing sulfur such as dimethylsulfoxide and sulfolane, and water.

The reaction proceeds more smoothly by adding a polymerization inhibitor such as hydroquinone in the presence of a base such as sodium hydrogen carbonate, potassium hydrogen carbonate, sodium carbonate or potassium carbonate.

After this, a target benzoic acid derivative can be produced in the same way as that in Process 2.

A compound of Formula (5), a starting material, can be prepared according to methods described, for example, in the following papers:

Chim. Ind. (Milan), 52 (1), 56 (1977): Preparation of 3-(1-propenyl)-1H-pyrrole;
Zh. Organ. Khim., 2, 417–423 (1966): Preparation of 5-(1-propenyl)-isoxazole;
J. Org. Chem., 62, 3671–3677 (1997): Preparation of 3(1-propenyl)-2-isoxazoline;
Heterocycles, 22 (11), 2475–2478 (1984): Preparation of 4(1-propenyl)pyridine; and
Heterocycles, 29(1), 103–114 (1989): Preparation of 5-(1-propenyl)-oxazole.

(Process 4)

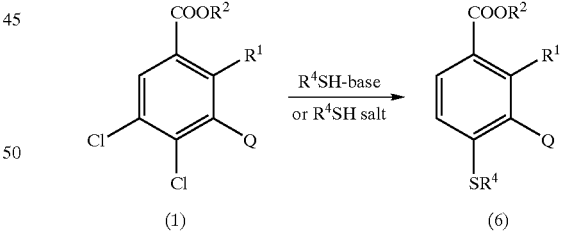

(wherein $R^1$, $R^2$, $R^4$ and Q are as defined above.)

In the process, a 4,5-dichlorobenzoic acid derivative of Formula (1) is reacted with an excessive amount of alkane thiol of Formula $R^4SH$ ($R^4$ is as defined above) in an appropriate inert solvent in the presence of a base, to give a 4-alkylthiobenzoic acid derivative of Formula (6).

While doing so, the reaction proceeds more smoothly under the irradiation of light (of a specified wavelength). Various light sources can be used, including sunlight, fluorescent lights, mercury lamps, arc lamps and incandescent lamps. It is preferable to carry out the reaction under inert gas atmosphere, after the reaction system is sufficiently degassed.

The reaction may sometimes proceed more smoothly by adding water of 0.1 to 5 times in equivalent to the amount of 4,5-dichlorobenzoic acid derivative (1).

Particularly preferred solvents used for this reaction are amides, such as dimethylformamide DMF), N,N-dimethylacetamide and N-methylpyrolidone. However, solvents used are not restricted to them.

Examples of bases used include hydroxides such as sodium hydroxide and potassium hydroxide; carbonates such as sodium carbonate, sodium hydrogen carbonate, potassium carbonate and potassium hydrogen carbonate; and metal alcolates such as sodium methylate, sodium etheylate and potassium t-butoxide. In this case, a salt of alkane thiol, such as sodium or potassium salt of alkane thiol, prepared from an alkane thiol and a base beforehand, can be used for the reaction.

Amounts of base and alkane thiol used are preferably 2 to 20 equivalents to that of 4,5-dichlorobenzoic acid derivative (1).

Benzoic acid derivatives of Formula (6) can be produced by isolation of Compound (7) followed by reduction, as shown in the following reaction scheme:

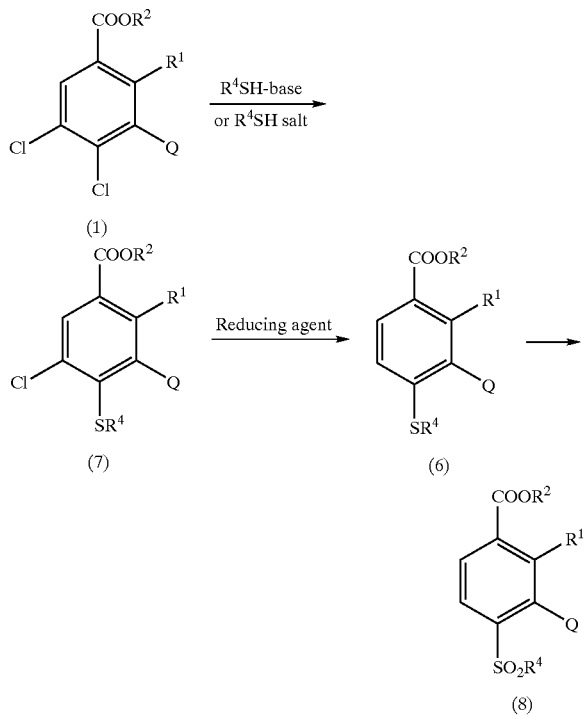

To produce a compound of Formula (7), an equivalent of a compound of Formula (1) is reacted with about 1 to 3 equivalents of an alkane thiol of Formula $R^4SH$ ($R^4$ is as defined above) in an inert solvent in the presence of an appropriate base.

In the reduction reaction from a compound of Formula (7) to a compound of Formula (6), the same alkane thiol ($R^4SH$) as that used in the previous reaction can be used as a reducing agent. Further, other reducing agents such as hydrogen sulfide and aromatic thiols can be employed.

A compound of Formula (6) can be derived to a corresponding $SO_2R^4$ compound (8) by oxidation reaction of the $SR^4$ group. This oxidation reaction may be carried out using an oxidizing agent including peroxides such as hydrogen peroxide, peracetic acid, perbenzoic acid and m-chloroperbenzoic acid, and hypochlorites such as sodium hypochlorite and potassium hypochlorite, in an inert solvent including water, alcohols such as methanol and ethanol organic acids such as acetic acid, and halogenated hydrocarbons such as dichloromethane, chloroform and carbon tetrachloride. The reaction proceeds smoothly in the temperature range from 0° C. to the boiling point of the solvent used.

Further, a $SO_2R^4$ compound (8) can be obtained by oxidation of a compound of the said Formula (7) and then a reduction reaction for dechlorination.

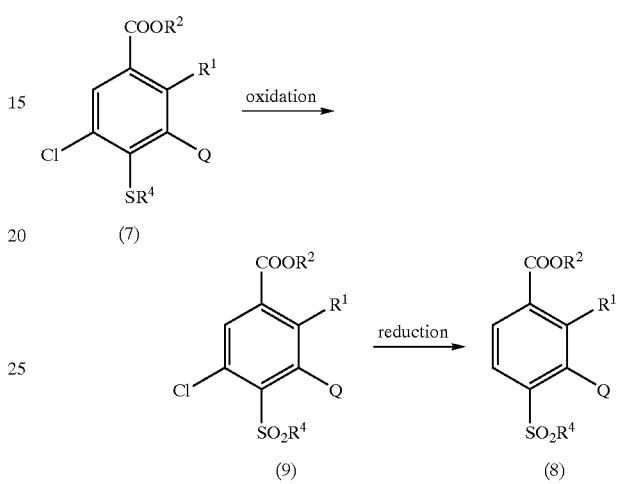

(wherein $R^1$, $R^2$, $R^4$ and Q are as defined above.)

A compound of Formula (9) can be produced by oxidation of a compound of Formula (7). This oxidation reaction may be carried out using an oxidizing agent including peroxides such as hydrogen peroxide, peracetic acid, perbenzoic acid and m-chloroperbenzoic acid, and hypochlorites such as sodium hypochlorite and potassium hypochlorite, in an inert solvent including water, alcohols such as methanol and ethanol, organic acids such as acetic acid, and halogenated hydrocarbons such as dichloromethane, chloroform and carbon tetrachloride. The reaction proceeds smoothly in the temperature range from 0° C. to the boiling point of the solvent used.

The next dechlorination of a compound of Formula (9) is carried out by such a method as catalytic hydrogenolysis using Raney nickel as a catalyst, method of using metal and metal salts such as lithium and sodium hydrogenolytic reduction with tin hydride, reduction with a metal-hydrogen complex compound such as lithium aluminum hydride, or electrolytic reduction, described in Shin Jikkenkagakukouza Vol. 14, Syntheses and Reactions of Organic Compounds [I] pages 22–30 (edited by the Chemical Society of Japan, published by Maruzen Co., Ltd.).

The compounds of the present invention, intermediates and others can be obtained with usual post-treatments after the completion of the reactions.

The structures of the compounds of the present invention, intermediates and others were determined by IR, NMR, MS and other means.

BEST FORM TO IMPLEMENT THE INVENTION

The present invention is described in more detail in reference to Examples and Reference Examples.

In Examples, of the compounds of the present invention, (1S, 4R, 5R, 6S) and (1R, 4S, 5S, 6R) isomers are represented as "trans", and (1S, 4R, 5R, 6R) and (1R, 4S, 5S, 6S) isomers as "cis".

EXAMPLE 1

Preparation of ethyl 4,5-dichloro-2-methyl-3-(3-methylisooxazol-5-yl)benzoate

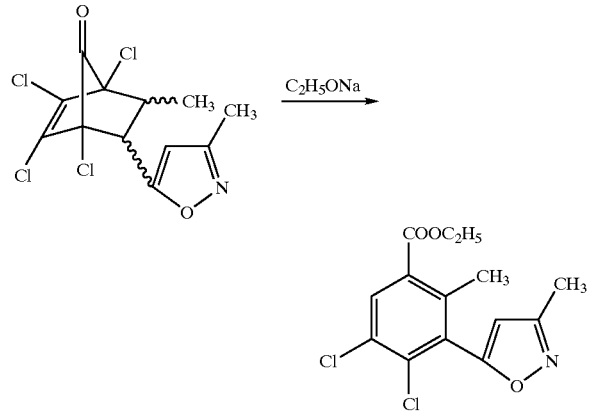

0.11 g of 6-methyl-5-(3-methylisoxazol-5-yl)-1,2,3,4-tetrachlorobicyclo[2.2.1]hept-2en-7-one (a mixture of trans:cis=1:1) was dissolved in 1 ml of ethanol, and 0.06 g of sodium ethylate was added, while cooling with ice. The resulting solution was stirred for an hour at room temperature. The reaction solution was poured into 50 ml of ice-water, and extracted with 30 ml of ethyl acetate twice. The organic layer was washed with saturated salt water and dried over anhydrous magnesium sulfate. The solvent was distilled off under reduced pressure. The obtained viscous liquid was purified on silica gel column chromatography (elution with n-hexane/ethyl acetate) to give 0.024 g of the title compound as white crystals. Melting point 86–88° C.

EXAMPLE 2

Preparation of methyl 4,5-dichloro-2-methyl-3-(3-methylisoxazol-5-yl)benzoate

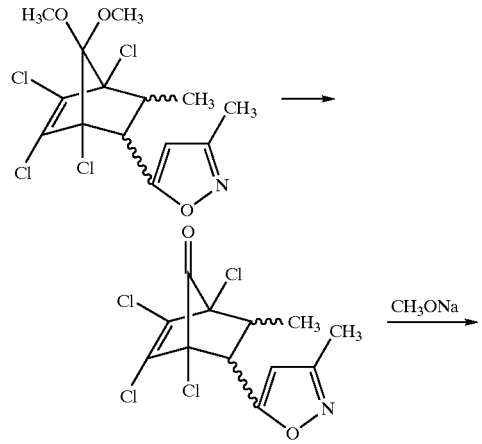

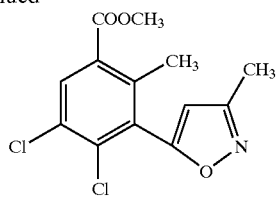

To 0.99 g of 6-methyl-cis-5-(3-methylisoxazol-5-yl)-7,7-dimethoxy-1,2,3,4-tetrachlorobicyclo[2.2]hept-2-ene was added 6.02 g of concentrated sulfuric acid, while cooling with ice. After returning to room temperature, the mixture was stirred for an hour. The resulting homogeneous solution was left undisturbed at room temperature for 15 hours. The reaction solution was poured into 20 ml of ice-water, and extracted with 20 ml of ethyl acetate twice. The organic layer was washed with aqueous sodium bicarbonate twice and then with saturated salt water, and dried over anhydrous magnesium sulfate. The magnesium sulfate was removed and the solvent was concentrated under reduced pressure to give 0.79 g of a crude product of 6-methyl-cis-5-(3-methylisoxazol-5-yl)-1,2,3,4-tetrachlorobicyclo[2.2.1]hept-2-en-7-one as a yellow sticky substance.

0.94 g of the obtained crude 6-methyl-cis-5-(3-methylisoxazol-5-yl)-1,2,3,4 tetrachlorobicyclo[2.2.1.]hept-2-en-7-one was dissolved in 10 ml of methanol, and 1.44 g of a 28% methanol solution of sodium methylate was dropped over 5 minutes, while cooling with ice. The resulting solution was stirred for 4 hours at room temperature, poured into 50 ml of ice-water, and extracted with 30 ml of ethyl acetate twice. The organic layer was washed with saturated salt water and dried over anhydrous magnesium sulfate. The solvent was concentrated under reduced pressure. The obtained viscous liquid was purified on silica gel column chromatography (elution with n-hexane/ethyl acetate) to give 0.42 g of the title compound as white crystals. Melting point: 76–77° C.

EXAMPLE 3

Preparation of 4,5-dichloro-2-methyl-5-(3-methylisoxazol-5-yl)benzoic acid

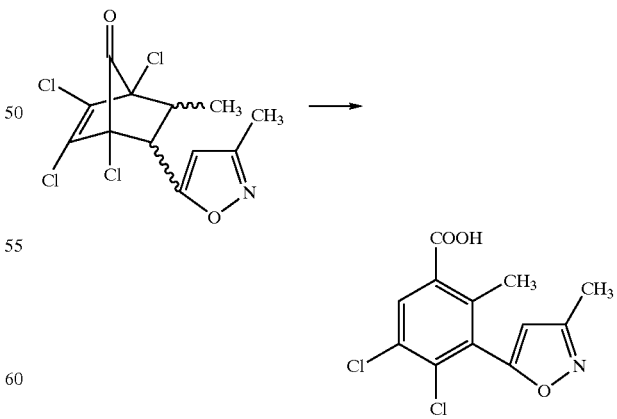

A solution of 156.9 g of 6-methyl-cis-5-(3-methylisoxazol-5-yl1,2,3,4-tetrachlorobicyclo[2.2.1]hept-2-en-7-one in 1150 ml of THF was dropped into a solution of 92 g of sodium hydroxide in 1150 ml of water at temperature between −3° C. and 0° C. over 1.5 hours. After the completion of the dropping, the cooling bath was removed. The reaction solution was stirred for 1.5 hours, while gradually rising the temperature to room temperature. After the reaction was completed, 500 ml of toluene was added to the reaction solution, and the aqueous layer was separated. Further, 500 ml of 1N aqueous solution of sodium hydroxide was added to the organic layer, and the aqueous layer was separated. The aqueous layers were combined, and 210 ml of concentrated hydrochloric acid was added to precipitate crystals. The crystals were separated by filtration, dissolved in 300 ml of ethyl acetate, and dried over anhydrous magnesium sulfate. The solvent was distilled off under reduced pressure to give 95.0 g of the title compound as white crystals. Melting point: 212–213° C.

EXAMPLE 4

Preparation of methyl 4,5-dichloro-2-methyl-3-(2-isoxazolin-3-yl)benzoate

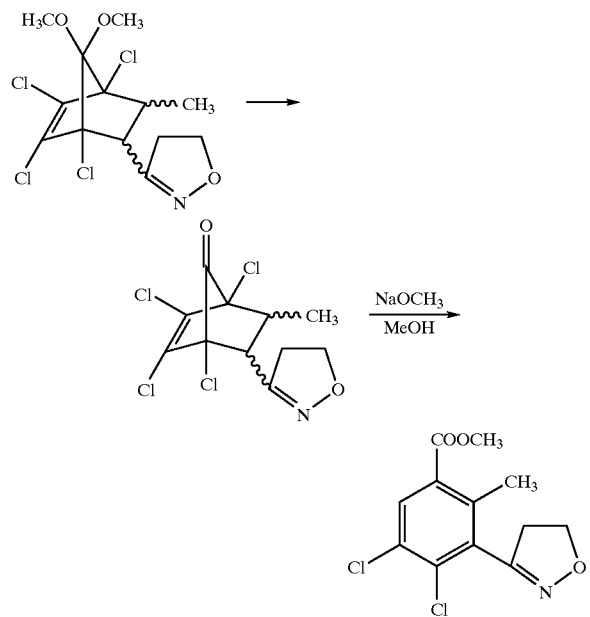

To 1.0 g of 6-methyl-cis-5-(2-isoxazolin-3-yl)-7,7-dimethoxy-1,2,3,4-tetrachlorobicyclo[2.2.1]hept-2-ene was added 6.3 g of concentrated sulfuric acid, while cooling with ice. After returning to room temperature, the mixture was stirred for an hour. The resulting homogeneous solution was left undisturbed at room temperature for 15 hours. The reaction solution was poured into 20 ml of ice-water and extracted with 20 ml of ethyl acetate twice. The organic layer was washed with aqueous sodium bicarbonate twice and then with saturated salt water, and dried over anhydrous magnesium sulfate. The magnesium sulfate was removed and the solvent was concentrated under reduced pressure to give 0.94 g of a crude product of 6-methyl-cis-5-(2-isoxazolin-3-yl)-1,2,3,4-tetrachlorobicyclo[2.2.1]hept-2-en-7-one as a yellow sticky substance.

0.94 g of the obtained crude product was dissolved in 10 ml of methanol, and 1.5 g of a 28% methanol solution of sodium methylate was dropped over 5 minutes, while cooling with ice. The resulting solution was stirred at room temperature for 2 hours. The reaction solution was poured into 50 ml of ice-water, and extracted with 30 ml of ethyl acetate twice. The organic layer was washed with saturated salt water and dried over anhydrous magnesium sulfate. The solvent was concentrated under reduced pressure. The obtained viscous liquid was purified on silica gel column chromatography (with development solvents: n-hexane/ethyl acetate) to give 0.71 g of the title compound as white crystals. Melting point: 74–76° C.

The above procedure was repeated to produce ethyl 4,5-dichloro-2-methyl-3-(2-isoxazolin-3-yl)benzoate. Melting point: 96–97° C.

EXAMPLE 5

Preparation of 4.5-dichloro-2-methyl-3-(2-isoxazolin-3-yl)benzoate

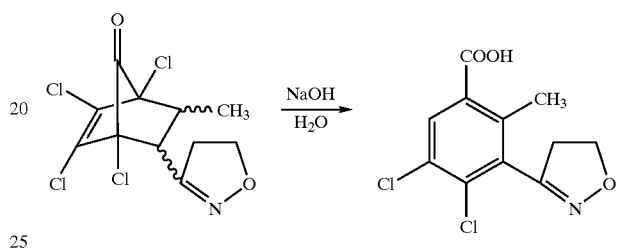

1.6 g of a crude product of 6-methyl-cis-5-(2-isoxazolin-3-yl)-1,2,3,4-tetrachlorobicyclo[2.2.1]hept-2-en-7-one, obtained in the same manner as that in Example 4, was dissolved in 5 ml of tetrahydrofuran and 5 ml of water, and 14.6 g of 1N aqueous solution of sodium hydroxide was dropped over 5 minutes, while cooling with ice. The resulting solution was stirred at room temperature for 2 hours. The reaction solution was poured into 50 ml of ice-water, acidified in pH with hydrochloric acid, and extracted with 30 ml of ethyl acetate twice. The organic layer was washed with saturated salt water, and dried over anhydrous magnesium sulfate. The solvent was concentrated under reduced pressure. The obtained crystals were washed with n-hexane to give 0.6 g of the title compound as white crystals. Melting point: 203–206° C.

EXAMPLE 6

Preparation of 6-methyl-cis-5-(3-methylisoxazol-5-yl)-7,7-dimethoxy-1,2,3,4-tetrachlorobicyclo[2.2.1]hept-2-ene

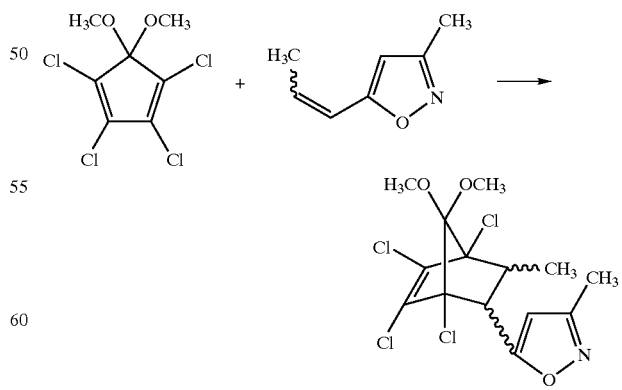

2.15 g of 5,5-dimethoxy-1,2,3,4-tetrachlorocyclopenta-1,3-diene, 0.81 g of sodium hydrogen carbonate, 1.00 g of 1-(3-methylisoxazol-5-yl)-1-propene (an equivalent mixture of trans and cis isomers), 0.40 g of zinc iodide and 0.10 g of hydroquinone were mixed and heated with stirring at 150° C. for 8 hours. The reaction solution was cooled and 100 ml of water was added. The resulting solution was extracted with 200 ml of ethyl acetate. Insoluble matter present was removed by filtration. The organic layer was washed with saturated salt water and dried over anhydrous magnesium sulfate. The solvent was concentrated under reduced pressure. n-Hexane was added to the obtained crude product. The precipitated crystals were separated by filtration to give 0.92 g of the title compound. Melting point: 100–101° C.

Further, the above filtrate was purified on silica gel column chromatography (elution with benzene) to give 0.74 g of the tide compound.

EXAMPLE 7

Preparation of 6-methyl-cis-5-(3-methylisoxazol-5-yl)-7,7-dimethoxy-1,2,3,4-tetrachlorobicyclo[2.2.1]hept-2-ene

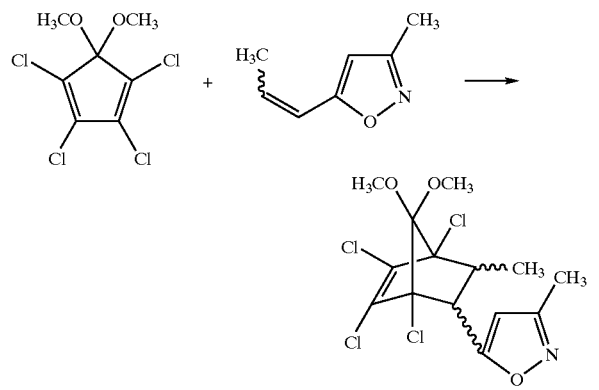

4.30 g of 5,5-dimethoxy-1,2,3,4-tetrachlorocyclopenta-1,3-diene, 1.00 g of 1-(3-methylisoxazol-5-yl)-1-propene (an equivalent mixture of trans and cis isomers) and 0.18 g of hydroquinone were added to 20 ml of 1,3-butanediol. The resulting mixture was heated at reflux for 7 hours. The reaction solution was cooled, poured into ice-water, and extracted with ethyl acetate. The organic layer was washed with saturated salt water, and dried over anhydrous magnesium sulfate. The solvent was concentrated under reduced pressure. n-Hexane was added to the obtained crude product. The separated viscous oil was removed. The n-hexane layer was concentrated under reduced pressure. The obtained crude product was purified on silica gel column chromatography (elution with benzene) to give 1.41 g of the title compound as white crystals. Melting point: 100–101° C.

EXAMPLE 8

Preparation of 6-methyl-5-(3-methylisoxazol-5-yl)-7,7-dimethoxy-1,2,3,4-tetrachlorobicyclo[2.2.1]hept-2-ene

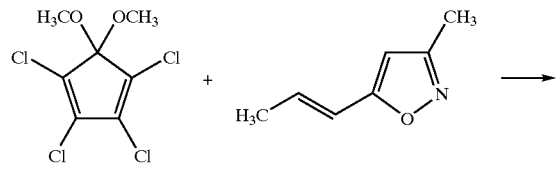

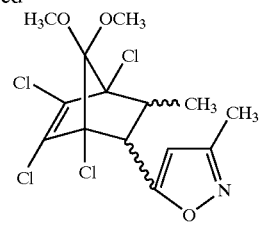

1.07 g of 5,5-dimethoxy-1,2,3,4-tetrachlorocyclopenta-1,3-diene, 0.34 g of sodium hydrogen carbonate, 0.50g of trans-1-(3-methylisoxazol-5-yl)-1-propene and 0.05 g of hydroquinone were mixed and heated with stirring at 180° C. for 7 hours. The reaction solution was cooled and ethyl acetate was added. Insoluble matter was removed by filtration. Then the solvent was concentrated under reduced pressure. The obtained crude product was purified on silica gel column chromatography (elution with benzene) to give 0.70 g of the title compound as a mixture of isomers.

EXAMPLE 9

Preparation of 6-methyl-cis-5-(3-methylisoxazol-5-yl)-7,7-dimethoxy-1,2,3,4-tetrachlorobicyclo[2.2.1]hept-2-ene

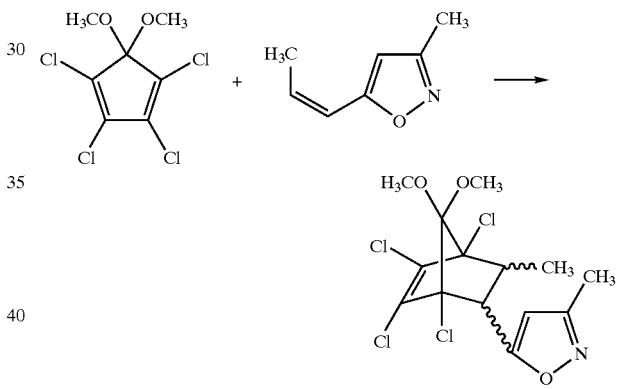

64.39 g of 5,5-dimethoxy-1,2,3,4-tetrachlorocyclopenta-1,3-diene, 14.07 g of sodium hydrogen carbonate, 20.00 g of cis-1-(3-methylisoxazol-5-yl)-1-propene and 2.00 g of hydroquinone were mixed and heated with stirring at 120° C. for 6 hours. The reaction solution was cooled and 500 ml of water was added. The resulting solution was extracted with ethyl acetate three times. Insoluble matter present was removed by filtration. The organic layer was washed with saturated salt water and dried over anhydrous magnesium sulfate.

The solvent was concentrated under reduced pressure. n-Hexane was added to the obtained crude product. The precipitated crystals were separated by filtration to give 45.81 g of the title compound. Melting point: 100–101° C.

Further, the filtrate after the filtration of the crystals was purified on silica gel column chromatography (elution with benzene) to give 4.50 g of the title compound.

$^1$H-NMR data of isomers (CDCl$_3$, δppm) cis isomer 0.83 (d, 3H), 2.30 (s, 3H), 3.08 (m, 1H), 3.58 (s, 3H), 3.66 (s, 3H), 4.17 (d, 1H), 6.02 (s, 1H) trans isomer-1

1.40 (d, 3H), 2.30 (s, 3H), 2.37 (m, 1H), 3.58 (s, 3H), 3.62 (d, 1H), 3.66 (s, 3H), 6.00 (s, 1H) trans isomer-2

1.09 (d, 3H), 2.34 (s, 3H), 2.84 (d, 1H), 3.07 (m, 1H), 3.50 (s, 3H), 3.57 (s, 3H), 6.19 (s, 1H)

EXAMPLE 10

Preparation of 6-methyl-cis-5-(2-isoxazolin-3-yl)-7,7-dimethoxy-1,2,3,4-tetrachlorobicyclo[2.2.1]hept-2-ene

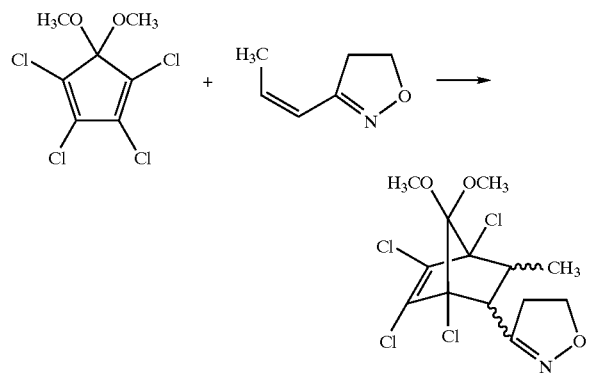

2.14 g of 5,5-dimethoxy-1,2,3,4-tetrachlorocyclopenta-1,3-diene, 0.46 g of sodium hydrogen carbonate and 0.6 g of cis-1-(2-isoxazolin-3-yl)-1-propene were mixed and heated with stirring at 120° C. for 6 hours. The reaction solution was cooled to room temperature and ice-water was added. The resulting solution was extracted with 200 ml of ethyl acetate. The organic layer was washed with water and dried over anhydrous magnesium sulfate. The solvent was concentrated under reduced pressure. The obtained oily product was purified on silica gel column chromatography (elution with n-hexane/ethyl acetate) to give 1.0 g of the title compound. Melting point: 98–100° C.

EXAMPLE 11

Preparation of 6-methyl-trans-5-(2-isoxazolin-3-yl)-7,7-dimethoxy-1,2,3,4-tetrachlorobicyclo[2.2.1]hept-2-ene

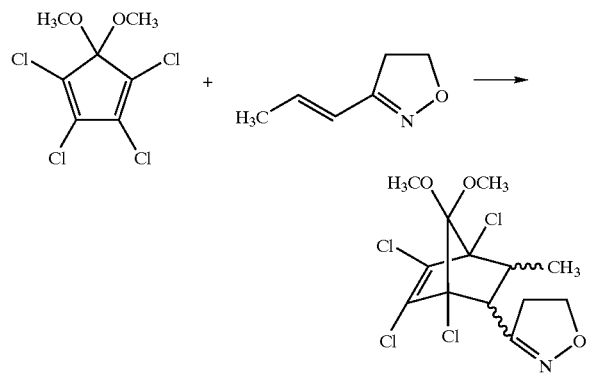

2.62 g of 5,5-dimethoxy-1,2,3,4-tetrachlorocyclopenta-1,3-diene, 1.1 g of sodium hydrogen carbonate and 1.0 g of trans-1-(2-isoxazolin-3-yl)-1-propene were mixed and heated with stirring at 200° C. for 20 hours. The reaction solution was cooled to room temperature, poured into ice-water, and extracted with ethyl acetate. The organic layer was washed with water and dried over anhydrous magnesium sulfate. The solvent was concentrated under reduced pressure. The obtained oily product was purified on silica gel column chromatography (elution with n-hexane/ethyl acetate) to give 1.8 g of the title compound. $n_D^{19.9}$ 1.5087

EXAMPLE 12

Preparation of ethyl 2-methyl-3-(3-methylisoxazol-5-yl)-4-methylthiobenzoate

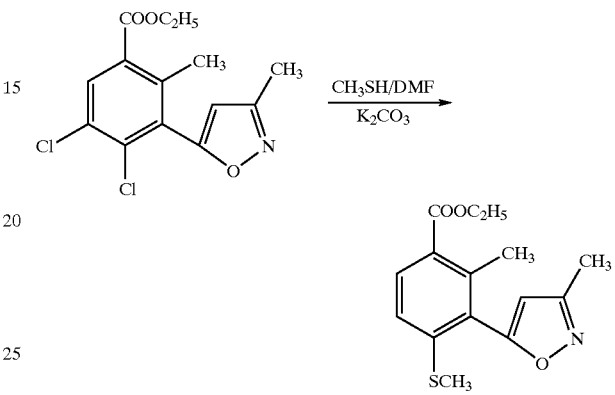

0.50 g of ethyl 4,5-dichloro-2-methyl-3-(3-methylisoxazol-5-yl)benzoate and 4.40 g of potassium carbonate were added to 15 ml of DMF, and a solution of 1.53 g of methyl mercaptan dissolved in 5 ml of DMF was dropped at room temperature. The resulting solution was further stirred for 19.5 hours. Then, the reaction solution was poured into ice-water and extracted with ethyl acetate. The organic layer was washed with water and then with saturated salt water, dried over anhydrous magnesium sulfate, and concentrated under reduced pressure. The obtained crude product was purified on silica gel column chromatography to give 0.42 g of the title compound as white crystals. Melting point: 72–74° C.

EXAMPLE 13

Preparation of ethyl 2-methyl-3-(3-methylisoxazol-5-yl)-4-methylthiobenzoate

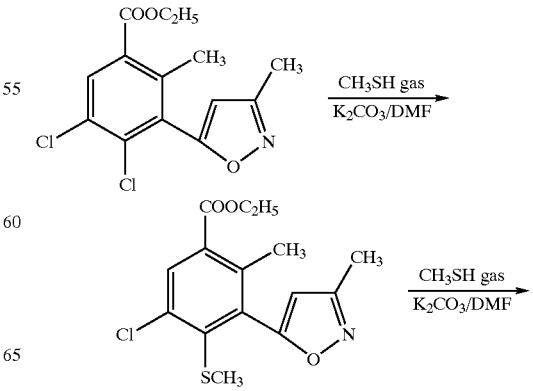

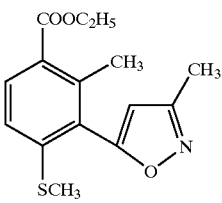

4.48 g of ethyl 4,5-dichloro-2-methyl-3-(3-methylisoxazol-5-yl)benzoate and 3.00 g of potassium carbonate were added to 100 ml of DMF, and 2.1 g of methyl mercaptan gas was blown into the reaction system at room temperature. The resulting solution was further stirred at room temperature for 15 hours. The reaction solution was poured into ice-water and extracted with ethyl acetate. The organic layer was washed with water and then with saturated salt water, dried over anhydrous magnesium sulfate, and concentrated under reduced pressure to give 4.40 g of ethyl 5-chloro-2-methyl-3-(3-methylisoxazol-5-yl)-4-methylthiobenzoate as white crystals. Melting point: 79–82° C.

0.50 g of the obtained ethyl 5-chloro-2-methyl-3-(3-methylisoxazol-5-yl)-4-methylthiobenzoate and 1.06 g of potassium carbonate were added to 15 ml of DMF, and further a solution of 0.36 g of methyl mercaptan dissolved in 5 ml of DMF was dropped at room temperature. The resulting solution was stirred at room temperature for 23 hours. The same procedure as that in Example 1 was repeated to give 0.29 g of the title compound as white crystals. 0.08 g of ethyl 5-chloro-2-methyl-3-(3-methylisoxazol-5-yl)-4-methylthiobenzoate was recovered.

EXAMPLE 14

Preparation of methyl 3-(2-isoxazolin-3-yl)-2-methyl-4-methylthiobenzoate

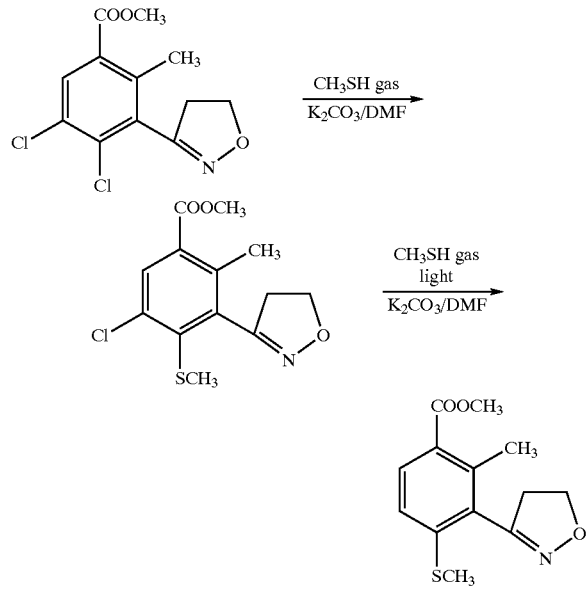

10 ml of degassed DMF was placed in a colorless, transparent glass container, and 420 mg of methyl mercaptan was blown in to dissolve. Then 600 mg of potassium carbonate and 500 mg of methyl 4,5-dichloro-3-(2-isoxazolin-3-yl)-2-methylbenzoate were added one by one. The resulting solution was stirred with a Teflon magnetic stirrer at room temperature with light shielded under the nitrogen atmosphere. After stirring it for an hour, it was confirmed by NMR that methyl 5-chloro-3-(2-isoxazolin-3-yl)-2-methyl-4-methylthiobenzoate was a major product. Succeedingly, the reaction system was stirred at 40° C. for 2 hours, while irradiating with white fluorescent light. The reaction solution was poured into ice-water, and extracted with ether-chloroform (5:1) and then with ether. The organic layers were washed with water, dried over sodium sulfate, and concentrated under reduced pressure. The obtained residue was purified on silica gel column chromatography (elution with n-hexane/ethyl acetate=95/5) to give 424 mg of the title compound as white crystals. Melting point: 109–111° C.

EXAMPLE 15

Preparation of t-butyl 2-methyl-3-(3-methylisoxazol-5-yl)-4-methylthiobenzoate

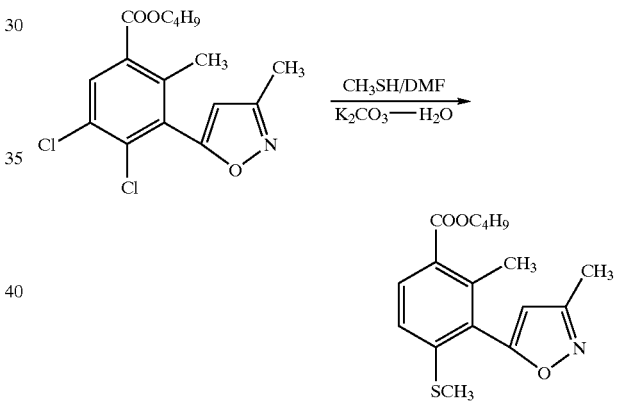

27 mg of water was added to 10 ml of DMF, and 360 mg of methyl mercaptan was blown into the resulting solution. Then the reaction system was purged by nitrogen. To the resulting solution were added 518 mg of potassium carbonate and 513 mg of t-butyl 4,5-dichloro-2-methyl-3-(3-methylisoxazol-5-yl)benzoate to stir at room temperature for 20 hours. The reaction solution was poured into 25 ml of ice-water and extracted with 25 ml of ether. The organic layer was washed with water and dried over anhydrous sodium sulfate. The solvent was distilled off under reduced pressure. The obtained crude product was purified on silica gel column chromatography (elution with n-hexane/ethyl acetate=95/5) to give 484 mg of the title compound with 83% purity as a white solid. (The purity was determined by NMR spectra.) The product was again purified on silica gel column chromatography to give the title compound with melting point of 102–103° C. as white crystals.

EXAMPLE 16

Preparation of ethyl 2-methyl-3-(2-isoxazolin-3-yl)-4-methylthiobenzoate

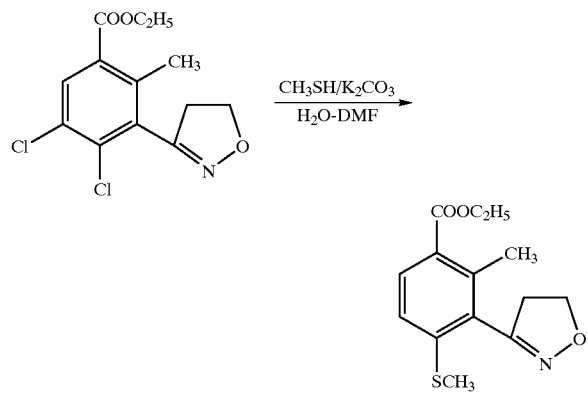

Into a 10-ml round-bottomed flask purged by nitrogen were placed 7.9 mg of water, 1.1 ml of DMF and a solution of 105 mg of methyl mercaptan in 1.5 ml of DMF, and then 151 mg of potassium carbonate and 132 mg of ethyl 4,5-dichloro-3-(2-isoxazol-3-yl)-2-methylbenzoate were added. The DMF used here was purged by nitrogen beforehand. The resulting mixture was stirred with a magnetic stirrer at room temperature for 3 hours and 45 minutes under the irradiation of 40W fluorescent light. The reaction solution was poured into 20 ml of ice-water, and extracted with 20 ml of diethyl ether. The organic layer was washed with water, and dried over anhydrous sodium sulfate. The solvent was distilled off under reduced pressure. The obtained crude product was purified on silica gel column chromatography (elution with n-hexane/ethyl acetate=95/5) to give 87.8 mg of the title compound as white crystals. Melting point: 93~94° C.

EXAMPLE 17

Preparation of ethyl 4-ethylthio-2-methyl-3-(3-methylisoxazol-5-yl)benzoate

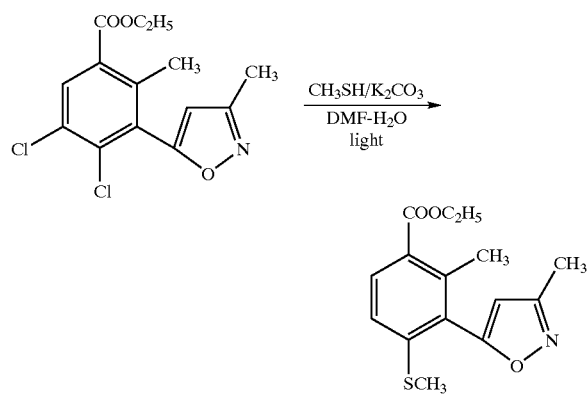

Into a 250-ml round-bottomed flask were placed 0.311 g of ethyl mercaptan, 0.018 g of water and 6 ml of DMF, and then 0.346 g of potassium carbonate and 0.314 g of ethyl 4,5-dichloro-2-methyl-3-(3-methylisoxazol-5-yl)benzoate were adder The resulting mixture was stirred with a magnetic stirrer at room temperature for 6 hours under the irradiation of 40W fluorescent light. The reaction solution was poured into 25 ml of ice-water, and extracted with 25 ml of diethyl ether. The organic layer was washed with water, and dried over anhydrous sodium sulfate. The solvent was distilled off under reduced pressure. The obtained crude product was purified on silica gel column chromatography (elution with n-hexane/ethyl acetate=95/5) to give 0.132 g of the title compound as white crystals. Melting point: 39–40° C.

The above procedure was repeated to produce methyl 4-methylthio-2-methyl-3-(3-methylisoxazol-5-yl)benzoate by reacting methyl 4,5-dichloro-2-methyl-3-(3-methylisoxazol-5-yl)benzoate and methyl mercaptan. Melting point: 94–95° C.

(REFERENCE EXAMPLES)

Examples of the preparation of the aforementioned 4-$SO_2R^4$ compounds (8) are described in reference to Reference Examples.

Reference Example 1

Preparation of ethyl 2-methyl-3-(3-methylisoxazol-5-yl)-4-methylsulfonylbenzoate

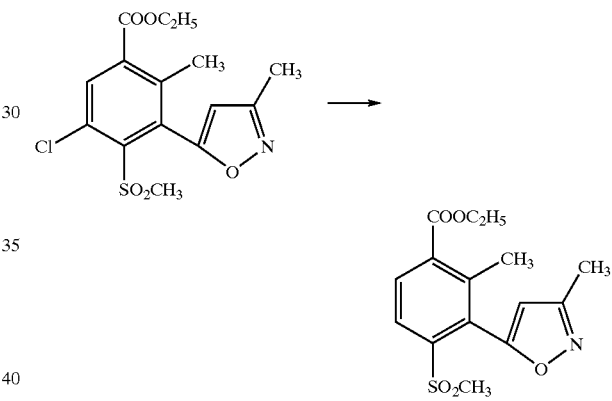

0.30 g of ethyl 5-chloro-2-methyl-3-(3-methylisoxazol-5-yl)-4-methylsulfonylbenzoate was dissolved in 20 ml of ethanol. After the reaction system was purged by nitrogen, 0.02 g of 5% palladium-carbon was added. The system was purged by hydrogen. A rubber ball filled with hydrogen was attached and the solution was stirred at room temperature for 3 hours. The palladium-carbon was removed from the reaction solution by filtration. The solvent was distilled off under reduced pressure to give 0.28 g of the title compound as white crystals. Melting point: 83–86° C.

Reference Example 2

Preparation of ethyl 5-chloro-2-methyl-3-(3-methylisoxazol-5-yl)-4-methylsulfonylbenzoate

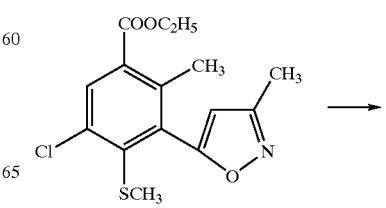

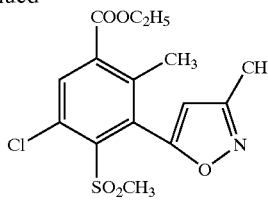

4.40 g of ethyl-5-chloro-2-methyl-3-(3-methylisoxazol-5-yl)-4-methylthiobenzoate was dissolved in 50 ml of chloroform, and 12.70 g of 55% m-chloroperbenzoic acid was added at room temperature. The resulting solution was stirred at room temperature for 19 hours. Precipitated crystals were separated from the reaction solution by filtration. The filtrate was washed with 80 ml of a 4% aqueous solution of sodium hydroxide. The organic layer was dried over anhydrous magnesium sulfate. The solvent was distilled off under reduced pressure to give 4.49 g of the title compound as white crystals. Melting point: 126–129° C.

Representative examples of the compounds of Formulae (1) and (2) of the present invention, including those in the above examples, are shown in Tables 1 and 2. The abbreviations of Q's in the tables have the following meanings:

Q1: isoxazol-5-yl, Q2: 3-methylisoxazol-5-yl, Q3: isoxazol-3-yl, Q4: 2-isoxazolin-3-yl, Q5: oxazol-2-yl, Q6: oxazol-4-yl, Q7: oxazol-5-yl, Q8: thiazol-2-yl, Q9: thiazol-4-yl, Q10: thiazol-5-yl, Q11: pyrazol-3-yl, Q12: 1-methyl-pyrazol-3-yl, Q13: 2-pyridyl, Q14: 3-pyridyl, Q15: 4-pyridyl, Q16: pyrimidin-2-yl, Q17: pyrimidin-4-yl, Q18: pyrimidin-5-yl, Q19: 1,3-dioxoran-2-yl, and Q20: 1,3-dioxan-2-yl

TABLE 1

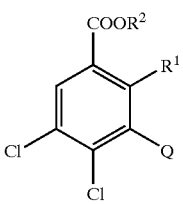

(1)

| Compound No. | Q |
|---|---|
| Table 1-1 | |
| $R^1$: $CH_3$ | |
| $R^2$: H | |
| 1-1 | Q1 |
| 1-2 | Q2 |
| 1-3 | Q3 |
| 1-4 | Q4 |
| 1-5 | Q5 |
| 1-6 | Q6 |
| 1-7 | Q7 |
| 1-8 | Q8 |
| 1-9 | Q9 |
| 1-10 | Q10 |
| 1-11 | Q11 |
| 1-12 | Q12 |
| 1-13 | Q13 |
| 1-14 | Q14 |
| 1-15 | Q15 |
| 1-16 | Q16 |
| 1-17 | Q17 |
| 1-18 | Q18 |
| 1-19 | Q19 |
| 1-20 | Q20 |
| Table 1-2 | |
| $R^1$: $CH_3$ | |
| $R^2$: $CH_3$ | |
| 1-21 | Q1 |
| 1-22 | Q2 |
| 1-23 | Q3 |
| 1-24 | Q4 |
| 1-25 | Q5 |
| 1-26 | Q6 |
| 1-27 | Q7 |
| 1-28 | Q8 |
| 1-29 | Q9 |
| 1-30 | Q10 |
| 1-31 | Q11 |
| 1-32 | Q12 |
| 1-33 | Q13 |
| 1-34 | Q14 |
| 1-35 | Q15 |
| 1-36 | Q16 |
| 1-37 | Q17 |
| 1-38 | Q18 |
| 1-39 | Q19 |
| 1-40 | Q20 |
| Table 1-3 | |
| $R^1$: $CH_3$ | |
| $R^2$: $C_2H_5$ | |
| 1-41 | Q1 |
| 1-42 | Q2 |
| 1-43 | Q3 |
| 1-44 | Q4 |
| 1-45 | Q5 |
| 1-46 | Q6 |
| 1-47 | Q7 |
| 1-48 | Q8 |
| 1-49 | Q9 |
| 1-50 | Q10 |
| 1-51 | Q11 |
| 1-52 | Q12 |
| 1-53 | Q13 |
| 1-54 | Q14 |
| 1-55 | Q15 |
| 1-56 | Q16 |
| 1-57 | Q17 |
| 1-58 | Q18 |
| 1-59 | Q19 |
| 1-60 | Q20 |
| Table 1-4 | |
| $R^1$: $CH_3$ | |
| $R^2$: n-$C_3H_7$ | |
| 1-61 | Q1 |
| 1-62 | Q2 |
| 1-63 | Q3 |
| 1-64 | Q4 |
| 1-65 | Q5 |
| 1-66 | Q6 |
| 1-67 | Q7 |
| 1-68 | Q8 |
| 1-69 | Q9 |
| 1-70 | Q10 |
| 1-71 | Q11 |
| 1-72 | Q12 |

TABLE 1-continued (1)

$$\text{structure: benzene ring with COOR}^2\text{, R}^1\text{, Q, and two Cl substituents}$$

| Compound No. | Q |
|---|---|
| 1-73 | Q13 |
| 1-74 | Q14 |
| 1-75 | Q15 |
| 1-76 | Q16 |
| 1-77 | Q17 |
| 1-78 | Q18 |
| 1-79 | Q19 |
| 1-80 | Q20 |

Table 1-5
$R^1$: $CH_3$
$R^2$: i-$C_3H_7$

| Compound No. | Q |
|---|---|
| 1-81 | Q1 |
| 1-82 | Q2 |
| 1-83 | Q3 |
| 1-84 | Q4 |
| 1-85 | Q5 |
| 1-86 | Q6 |
| 1-87 | Q7 |
| 1-88 | Q8 |
| 1-89 | Q9 |
| 1-90 | Q10 |
| 1-91 | Q11 |
| 1-92 | Q12 |
| 1-93 | Q13 |
| 1-94 | Q14 |
| 1-95 | Q15 |
| 1-96 | Q16 |
| 1-97 | Q17 |
| 1-98 | Q18 |
| 1-99 | Q19 |
| 1-100 | Q20 |

Table 1-6
$R^1$: $CH_3$
$R^2$: n-$C_4H_9$

| Compound No. | Q |
|---|---|
| 1-101 | Q1 |
| 1-102 | Q2 |
| 1-103 | Q3 |
| 1-104 | Q4 |
| 1-105 | Q5 |
| 1-106 | Q6 |
| 1-107 | Q7 |
| 1-108 | Q8 |
| 1-109 | Q9 |
| 1-110 | Q10 |
| 1-111 | Q11 |
| 1-112 | Q12 |
| 1-113 | Q13 |
| 1-114 | Q14 |
| 1-115 | Q15 |
| 1-116 | Q16 |
| 1-117 | Q17 |
| 1-118 | Q18 |
| 1-119 | Q19 |
| 1-120 | Q20 |

Table 1-7
$R^1$: $CH_3$
$R^2$: n-$C_4H_9$ᵃ

| Compound No. | Q |
|---|---|
| 1-121 | Q1 |
| 1-122 | Q2 |
| 1-123 | Q3 |
| 1-124 | Q4 |
| 1-125 | Q5 |
| 1-126 | Q6 |
| 1-127 | Q7 |
| 1-128 | Q8 |
| 1-129 | Q9 |
| 1-130 | Q10 |
| 1-131 | Q11 |
| 1-132 | Q12 |
| 1-133 | Q13 |
| 1-134 | Q14 |
| 1-135 | Q15 |
| 1-136 | Q16 |
| 1-137 | Q17 |
| 1-138 | Q18 |
| 1-139 | Q19 |
| 1-140 | Q20 |

Table 1-8
$R^1$: $CH_3$
$R^2$: t-$C_4H_9$

| Compound No. | Q |
|---|---|
| 1-141 | Q1 |
| 1-142 | Q2 |
| 1-143 | Q3 |
| 1-144 | Q4 |
| 1-145 | Q5 |
| 1-146 | Q6 |
| 1-147 | Q7 |
| 1-148 | Q8 |
| 1-149 | Q9 |
| 1-150 | Q10 |
| 1-151 | Q11 |
| 1-152 | Q12 |
| 1-153 | Q13 |
| 1-154 | Q14 |
| 1-155 | Q15 |
| 1-156 | Q16 |
| 1-157 | Q17 |
| 1-158 | Q18 |
| 1-159 | Q19 |
| 1-160 | Q20 |

Table 1-9
$R^1$: $CH_3$
$R^2$: i-$C_5H_{11}$

| Compound No. | Q |
|---|---|
| 1-161 | Q1 |
| 1-162 | Q2 |
| 1-163 | Q3 |
| 1-164 | Q4 |
| 1-165 | Q5 |
| 1-166 | Q6 |
| 1-167 | Q7 |
| 1-168 | Q8 |
| 1-169 | Q9 |
| 1-170 | Q10 |
| 1-171 | Q11 |
| 1-172 | Q12 |
| 1-173 | Q13 |
| 1-174 | Q14 |
| 1-175 | Q15 |
| 1-176 | Q16 |
| 1-177 | Q17 |
| 1-178 | Q18 |
| 1-179 | Q19 |
| 1-180 | Q20 |

TABLE 1-continued (1)

Structure: benzene ring with COOR² (top), R¹ (ortho to COOR²), Q (meta to COOR², between the two Cl groups), and two Cl substituents.

| Compound No. | Q |
|---|---|
| Table 1-10 | |
| R¹: CH₃ | |
| R²: t-C₅H₁₁ | |
| 1-181 | Q1 |
| 1-182 | Q2 |
| 1-183 | Q3 |
| 1-184 | Q4 |
| 1-185 | Q5 |
| 1-186 | Q6 |
| 1-187 | Q7 |
| 1-188 | Q8 |
| 1-189 | Q9 |
| 1-190 | Q10 |
| 1-191 | Q11 |
| 1-192 | Q12 |
| 1-193 | Q13 |
| 1-194 | Q14 |
| 1-195 | Q15 |
| 1-196 | Q16 |
| 1-197 | Q17 |
| 1-198 | Q18 |
| 1-199 | Q19 |
| 1-200 | Q20 |
| Table 1-11 | |
| R¹: C₂H₅ | |
| R²: H | |
| 1-201 | Q1 |
| 1-202 | Q2 |
| 1-203 | Q3 |
| 1-204 | Q4 |
| 1-205 | Q5 |
| 1-206 | Q6 |
| 1-207 | Q7 |
| 1-208 | Q8 |
| 1-209 | Q9 |
| 1-210 | Q10 |
| 1-211 | Q11 |
| 1-212 | Q12 |
| 1-213 | Q13 |
| 1-214 | Q14 |
| 1-215 | Q15 |
| 1-216 | Q16 |
| 1-217 | Q17 |
| 1-218 | Q18 |
| 1-219 | Q19 |
| 1-220 | Q20 |
| Table 1-12 | |
| R¹: C₂H₅ | |
| R²: CH₃ | |
| 1-221 | Q1 |
| 1-222 | Q2 |
| 1-223 | Q3 |
| 1-224 | Q4 |
| 1-225 | Q5 |
| 1-226 | Q6 |
| 1-227 | Q7 |
| 1-228 | Q8 |
| 1-229 | Q9 |
| 1-230 | Q10 |
| 1-231 | Q11 |
| 1-232 | Q12 |
| 1-233 | Q13 |
| 1-234 | Q14 |
| 1-235 | Q15 |
| 1-236 | Q16 |
| 1-237 | Q17 |
| 1-238 | Q18 |
| 1-239 | Q19 |
| 1-240 | Q20 |
| Table 1-13 | |
| R¹: C₂H₅ | |
| R²: C₂H₅ | |
| 1-241 | Q1 |
| 1-242 | Q2 |
| 1-243 | Q3 |
| 1-244 | Q4 |
| 1-245 | Q5 |
| 1-246 | Q6 |
| 1-247 | Q7 |
| 1-248 | Q8 |
| 1-249 | Q9 |
| 1-250 | Q10 |
| 1-251 | Q11 |
| 1-252 | Q12 |
| 1-253 | Q13 |
| 1-254 | Q14 |
| 1-255 | Q15 |
| 1-256 | Q16 |
| 1-257 | Q17 |
| 1-258 | Q18 |
| 1-259 | Q19 |
| 1-260 | Q20 |
| Table 1-14 | |
| R¹: C₂H₅ | |
| R²: n-C₃H₇ | |
| 1-261 | Q1 |
| 1-262 | Q2 |
| 1-263 | Q3 |
| 1-264 | Q4 |
| 1-265 | Q5 |
| 1-266 | Q6 |
| 1-267 | Q7 |
| 1-268 | Q8 |
| 1-269 | Q9 |
| 1-270 | Q10 |
| 1-271 | Q11 |
| 1-272 | Q12 |
| 1-273 | Q13 |
| 1-274 | Q14 |
| 1-275 | Q15 |
| 1-276 | Q16 |
| 1-277 | Q17 |
| 1-278 | Q18 |
| 1-279 | Q19 |
| 1-280 | Q20 |
| Table 1-15 | |
| R¹: C₂H₅ | |
| R²: i-C₃H₇ | |
| 1-281 | Q1 |
| 1-282 | Q2 |
| 1-283 | Q3 |
| 1-284 | Q4 |
| 1-285 | Q5 |
| 1-286 | Q6 |

TABLE 1-continued (1)

Structure: benzene ring with COOR² (top), R¹ (right), Q (bottom right), Cl (bottom left), Cl (left)

| Compound No. | Q |
|---|---|
| 1-287 | Q7 |
| 1-288 | Q8 |
| 1-289 | Q9 |
| 1-290 | Q10 |
| 1-291 | Q11 |
| 1-292 | Q12 |
| 1-293 | Q13 |
| 1-294 | Q14 |
| 1-295 | Q15 |
| 1-296 | Q16 |
| 1-297 | Q17 |
| 1-298 | Q18 |
| 1-299 | Q19 |
| 1-300 | Q20 |

Table 1-16
$R^1$: $C_2H_5$
$R^2$: n-$C_4H_9$

| Compound No. | Q |
|---|---|
| 1-301 | Q1 |
| 1-302 | Q2 |
| 1-303 | Q3 |
| 1-304 | Q4 |
| 1-305 | Q5 |
| 1-306 | Q6 |
| 1-307 | Q7 |
| 1-308 | Q8 |
| 1-309 | Q9 |
| 1-310 | Q10 |
| 1-311 | Q11 |
| 1-312 | Q12 |
| 1-313 | Q13 |
| 1-314 | Q14 |
| 1-315 | Q15 |
| 1-316 | Q16 |
| 1-317 | Q17 |
| 1-318 | Q18 |
| 1-319 | Q19 |
| 1-320 | Q20 |

Table 1-17
$R^1$: $C_2H_5$
$R^2$: s-$C_4H_9$

| Compound No. | Q |
|---|---|
| 1-321 | Q1 |
| 1-322 | Q2 |
| 1-323 | Q3 |
| 1-324 | Q4 |
| 1-325 | Q5 |
| 1-326 | Q6 |
| 1-327 | Q7 |
| 1-328 | Q8 |
| 1-329 | Q9 |
| 1-330 | Q10 |
| 1-331 | Q11 |
| 1-332 | Q12 |
| 1-333 | Q13 |
| 1-334 | Q14 |
| 1-335 | Q15 |
| 1-336 | Q16 |
| 1-337 | Q17 |
| 1-338 | Q18 |
| 1-339 | Q19 |
| 1-340 | Q20 |

Table 1-18
$R^1$: $C_2H_5$
$R^2$: t-$C_4H_9$

| Compound No. | Q |
|---|---|
| 1-341 | Q1 |
| 1-342 | Q2 |
| 1-343 | Q3 |
| 1-344 | Q4 |
| 1-345 | Q5 |
| 1-346 | Q6 |
| 1-347 | Q7 |
| 1-348 | Q8 |
| 1-349 | Q9 |
| 1-350 | Q10 |
| 1-351 | Q11 |
| 1-352 | Q12 |
| 1-353 | Q13 |
| 1-354 | Q14 |
| 1-355 | Q15 |
| 1-356 | Q16 |
| 1-357 | Q17 |
| 1-358 | Q18 |
| 1-359 | Q19 |
| 1-360 | Q20 |

Table 1-19
$R^1$: $C_2H_5$
$R^2$: i-$C_5H_{11}$

| Compound No. | Q |
|---|---|
| 1-361 | Q1 |
| 1-362 | Q2 |
| 1-363 | Q3 |
| 1-364 | Q4 |
| 1-365 | Q5 |
| 1-366 | Q6 |
| 1-367 | Q7 |
| 1-368 | Q8 |
| 1-369 | Q9 |
| 1-370 | Q10 |
| 1-371 | Q11 |
| 1-372 | Q12 |
| 1-373 | Q13 |
| 1-374 | Q14 |
| 1-375 | Q15 |
| 1-376 | Q16 |
| 1-377 | Q17 |
| 1-378 | Q18 |
| 1-379 | Q19 |
| 1-380 | Q20 |

Table 1-20
$R^1$: $C_2H_5$
$R^2$: t-$C_5H_{11}$

| Compound No. | Q |
|---|---|
| 1-381 | Q1 |
| 1-382 | Q2 |
| 1-383 | Q3 |
| 1-384 | Q4 |
| 1-385 | Q5 |
| 1-386 | Q6 |
| 1-387 | Q7 |
| 1-388 | Q8 |
| 1-389 | Q9 |
| 1-390 | Q10 |
| 1-391 | Q11 |
| 1-392 | Q12 |
| 1-393 | Q13 |

TABLE 1-continued

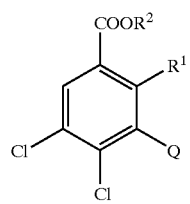

(1)

| Compound No. | Q |
|---|---|
| 1-394 | Q14 |
| 1-395 | Q15 |
| 1-396 | Q16 |
| 1-397 | Q17 |
| 1-398 | Q18 |
| 1-399 | Q19 |
| 1-400 | Q20 |

TABLE 2

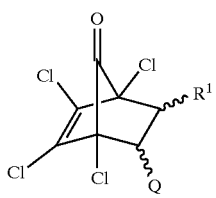

(2)

| Compound No. | Q |
|---|---|
| Table 2-1 $R^1$: $CH_3$ | |
| 2-1 | Q1 |
| 2-2 | Q2 |
| 2-3 | Q3 |
| 2-4 | Q4 |
| 2-5 | Q5 |
| 2-6 | Q6 |
| 2-7 | Q7 |
| 2-8 | Q8 |
| 2-9 | Q9 |
| 2-10 | Q10 |
| 2-11 | Q11 |
| 2-12 | Q12 |
| 2-13 | Q13 |
| 2-14 | Q14 |
| 2-15 | Q15 |
| 2-16 | Q16 |
| 2-17 | Q17 |
| 2-18 | Q18 |
| 2-19 | Q19 |
| 2-20 | Q20 |
| Table 2-2 $R^1$: $C_2H_5$ | |
| 2-21 | Q1 |
| 2-22 | Q2 |
| 2-23 | Q3 |
| 2-24 | Q4 |
| 2-25 | Q5 |
| 2-26 | Q6 |
| 2-27 | Q7 |
| 2-28 | Q8 |
| 2-29 | Q9 |
| 2-30 | Q10 |
| 2-31 | Q11 |
| 2-32 | Q12 |
| 2-33 | Q13 |
| 2-34 | Q14 |

TABLE 2-continued

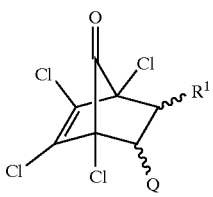

(2)

| Compound No. | Q |
|---|---|
| 2-35 | Q15 |
| 2-36 | Q16 |
| 2-37 | Q17 |
| 2-38 | Q18 |
| 2-39 | Q19 |
| 2-40 | Q20 |

TABLE 3

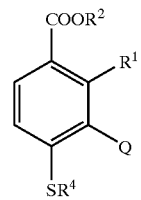

(6)

Table 3-1
Compounds 3-1 to 3-400, where $R^4$ is $CH_3$, that are derived from Compounds Nos. from 1-1 to 1-400 in Table 1.
Table 3-2
Compounds 3-401 to 3-800, where $R^4$ is $C_2H_5$, that are derived from Compounds Nos. from 1-1 to 1-400 in Table 1.
Table 3-3
Compounds 3-801 to 3-1200, where $R^4$ is i-$C_3H_7$, that are derived from Compounds Nos. from 1-1 to 1-400 in Table 1.
Table 3-4
Compounds 3-1201 to 3-1600, where $R^4$ is t-$C_4H_9$, that are derived from Compounds Nos. from 1-1 to 1-400 in Table 1.

Applicability in Industry

As described above, according to the present invention, benzoic acid derivatives useful as intermediates for the preparation of agricultural chemicals and drugs, particularly compounds having herbicidal activity, can be produced simply, easily and industrially advantageously in a short process, using inexpensive cyclopentadiene derivatives and ethylene derivatives substituted with hetero rings as starting materials.

For example, reactions of compounds of Formula (6), which are produced according to the present invention, with 3-hydroxypyrazoles give herbicides disclosed in WO 96/26206, WO 97/41118 and others.

What is claimed is:
1. A process for the preparation of a substituted benzoic acid of Formula (1)

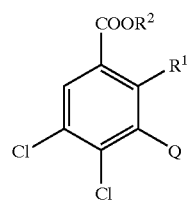

(1)

wherein R¹ is hydrogen or $C_{1-4}$ alkyl, R² is hydrogen or $C_{1-6}$ alkyl, and Q is an optionally substituted, saturated or unsaturated, 5- or 6-membered heterocyclic group wherein said heterocyclic group is selected from the group consisting of:

a) a five member heterocyclic ring having at least one heteroatom which is selected from the group consisting of N, O, or S, and where the heterocyclic group is linked to the benzene ring via a carbon atom; or b) a six member heterocyclic ring having at least one heteroatom which is selected from the group consisting of N, O, or S, and where the heterocyclic group is linked to the benzene ring via a carbon atom;

which comprises reacting a substituted bicycloheptenone of Formula (2)

(2)

wherein R¹ is as defined above and Q

Q-1

Q-2

Q-3

Q-4

Q-5

Q-6

Q-7

Q-8

-continued

Q-9 is an optionally substituted, saturated or unsaturated, 5- or 6-membered heterocyclic group wherein said heterocyclic group is selected from the group consisting of:

a) a five member heterocyclic ring having at least one heteroatom which is selected from the group consisting of N, O, or S, and where the heterocyclic group is linked to the benzene ring via a carbon atom; or b) a six member heterocyclic ring having at least one heteroatom which is selected from the group consisting of N, O, or S, and where the heterocyclic group is linked to the benzene ring via a carbon atom;

with a base and water or alcohol of Formula $R_2OH$, wherein $R_2$ is hydrogen or $C_{1-6}$ alkyl, in an appropriate solvent, and wherein the base is an alkali metal alkoxide, all alkali metal hydroxide or an alkaline earth metal hydroxide, the alcohol is methanol, ethanol, propanol, isopropanol, butanol or t-butanol, and the solvent is methanol, ethanol, propanol, isopropanol, butanol or t-butanol, or THF.

2. A process for the preparation of a substituted benzoic acid of Formula (1)

(1)

wherein R¹ is hydrogen or $C_{1-4}$ alkyl, R² is hydrogen or $C_{1-6}$ alkyl, and Q is selected from the group consisting of Q-1, Q-2, Q-3, Q-4, Q-5, Q-6, Q-7, Q-8 and Q-9

Q-1

Q-2

Q-3

Q-4

Q-5

Q-6

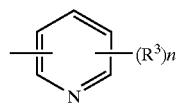

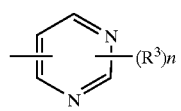

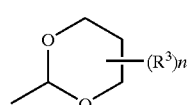

wherein $R^3$ is $C_{1-4}$ alkyl or $C_{1-4}$ haloalkyl, and n is 0 or an integer of 1 or 2, which comprises having a stage for the preparation of a substituted bicycloheptenone of Formula (2)

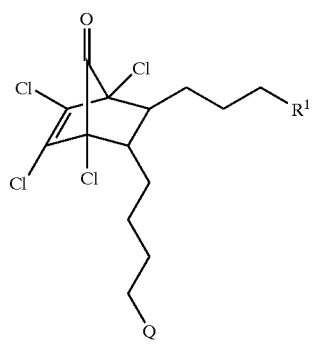

(2)

wherein $R^1$ and Q are as defined above by hydrolysis of a substituted bicycloheptene of Formula (3)

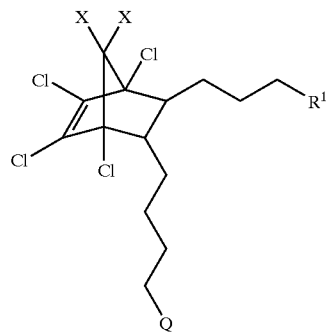

(3)

wherein $R^1$ and Q are as defined above, and X is chlorine or $C_{1-4}$ alkoxy; and the two X's may join together to form a $C_{2-3}$ alkylenedioxy group optionally substituted with $C_{1-4}$ alkyl, and a stage of reacting the substituted bicycloheptenone of the above Formula (2) with a base and water or alcohol in an appropriate solvent, and wherein the base is an alkali metal alkoxide, an alkali metal hydroxide or an alkaline earth metal hydroxide, the alcohol is methanol, ethanol, propanol, isopropanol, butanol or t-butanol, and the solvent is methanol, ethanol, propanol, isopropanol, butanol or t-butanol, or THF.

3. A process for the preparation of a substituted benzoic acid of the above Formula (1) according to claim 1, in which the base is one or more compounds selected from the group consisting of alkali metal alkoxides, alkali metal hydroxides and alkaline earth metal hydroxides.

4. A process according to claim 1, in which the solvent is an alcohol or a solvent containing an alcohol.

5. A process according to claim 2, in which the hetero ring represented by Q is a group selected from the following group consisting of Q-1, Q-2, Q-3, Q-4, Q-5, Q-6, Q-7, Q-8 and Q-9

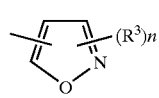 Q-1

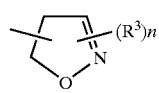 Q-2

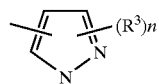 Q-3

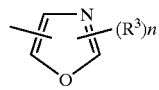 Q-4

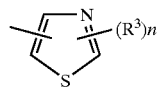 Q-5

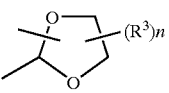 Q-6

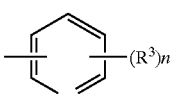 Q-7

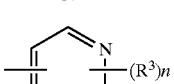 Q-8

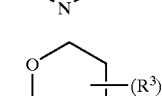 Q-9 wherein $R^3$ is $C_{1-4}$ alkyl or $C_{1-4}$ haloalkyl, and n is 0 or an integer of 1 or 2.

* * * * *